United States Patent [19]
Juji et al.

[11] Patent Number: 5,264,340
[45] Date of Patent: Nov. 23, 1993

[54] CELL SURFACE ANTIGEN DETERMINATION METHOD FOR DETERMINING AN IMMUNOCYTE IN A COMPLEXED ANTIGEN-ANTIBODY REACTION SYSTEM

[75] Inventors: Takeo Juji, Chiba; Choku Matsuhashi, Saitama; Masao Takahashi; Toshihiko Tazawa, both of Tokyo, all of Japan

[73] Assignee: Technology Research Association of Medical and Welfare Apparatus, Tokyo, Japan

[21] Appl. No.: 492,167

[22] Filed: Mar. 13, 1990

[30] Foreign Application Priority Data

Mar. 28, 1989 [JP] Japan .................................. 1-75769

[51] Int. Cl.⁵ .................. G01N 33/53; G01N 33/543; G01N 33/558
[52] U.S. Cl. ..................................... 435/7.2; 435/7.24; 436/512; 436/514; 436/518; 436/538; 436/824
[58] Field of Search ................ 435/7.2, 7.24; 436/512, 436/514, 518, 538, 824

[56] References Cited

U.S. PATENT DOCUMENTS

4,721,681  1/1988  Lentrichia et al. .................. 436/518

FOREIGN PATENT DOCUMENTS

0157197  3/1985  European Pat. Off. .
8701810  3/1987  European Pat. Off. .
0358758  3/1990  European Pat. Off. .
0235337  4/1986  Fed. Rep. of Germany ....... 435/7.2

*Primary Examiner*—David Saunders
*Assistant Examiner*—Christopher L. Chin
*Attorney, Agent, or Firm*—Sughrue, Mion, Zinn, Macpeak & Seas

[57] ABSTRACT

A cell surface antigen determination method for determining an immunocyte having an immune antigen-antibody complex composed of an antigen and an antibody combined therewith in a liquid which contains immunocytes having various antigens and also containing many kinds of antibodies, and an apparatus used in this method. In accordance with the inventive method and apparatus, non-specific reactions are restrained so as to reduce the background without using a complement.

1 Claim, 4 Drawing Sheets

CELL SURFACE ANTIGEN DETERMINATION METHOD FOR DETERMINING AN IMMUNOCYTE IN A COMPLEXED ANTIGEN-ANTIBODY REACTION SYSTEM

BACKGROUND OF THE INVENTION

The present invention relates to a cell surface antigen determination method for determining an immunocyte having an immune antigen-antibody complex composed of an antigen and an antibody combined therewith in a liquid which contains immunocytes having various antigens and also containing many kinds of antibodies. The invention also relates to an apparatus used in this method.

The following are general conventional methods for immune reaction:
1. Qualitative techniques such as a ring test, a capillary test, a tube test, an immune diffusion test, and quantitative techniques such as a quantitative precipitation method, a laser nephelometry, and a quantitative immune diffusion method.
2. Hemolysis and bacteriolysis assays.
3. Agglutination techniques such as a cell agglutination test, an anti-globulin test (Coombs test), a passive hemagglutination method (PHA, HA), and an immune adherence method (IA).
4. Passive cutaneous anaphylaxis assay (PCA).
5. Labeled antibody techniques such as fluoroimmunoassay (FIA), enzyme immunoassay (EIA), and radio immunoassay (RIA).

The above methods have been improved in various ways depending on their applications, and automation and labor-saving techniques have been achieved with respect to these methods. However, in a general immune reaction, in the absence of a monoclonal antibody of a highly specific nature or a complement, or even in the presence of a complement, the complement activity in many cases is not efficient. In such a case, a background increase due to non-specific reactions and other factors cannot be disregarded, and as a result it is very difficult to determine an intended specific reaction.

For example, the following problems are encountered with a lymphocyte cytotoxicity test (LCT) of a human leukocyte antigen system A (HLA) based on hemolysis and bacteriolysis assays. In this test, an antiserum which is derived from a multipara and has various specificities and activities is used as an antibody, and this antibody is reacted with a lymphocyte HLA antigen to determine the HLA type. In this case, a complement, which is specifically activated in cytotoxicity under the influence of an immune antigen-antibody complex produced as a result of the reaction, and a coloring matter for dyeing destroyed lymphocytes are used. The degree of specificity of the lymphocyte is evaluated from the color matter-dyeing frequency proportional to the immunocyte cytotoxicity frequency. However, when the antigen concentration is low, for example, in the case where the antigen is diffused at the surface of one lymphocyte, the complement activity is not sufficient. Also, in IgG4 sub-class antibody reactions, complement activity is not found. In such a case, it is very difficult to determine the specificity of the lymphocyte. Further, although more than 140 kinds of HLA antigens have been discovered, much larger numbers are believed to exist. However, no determination method has yet been established.

SUMMARY OF THE INVENTION

In view of the above, it is an object of the invention to determine an immunocyte having an immune antigen-antibody complex by restraining a non-specific reaction so as to reduce the background without using a complement.

According to the present invention, there is provided a method for determining a cell surface antigen in a complexed antigen-antibody reaction system, comprising the steps of:
securing a substance capable of specifically binding to immunoglobulin to part of an inner surface of a container;
introducing a first liquid and a second liquid into the container, the first liquid containing an immunocyte having at its surface an immune antigen-antibody complex composed of an antigen and an antibody combined with the antigen, the second liquid being higher in specific gravity than the first liquid;
rotating the container in such a manner so that the part of the inner surface is disposed most remote from the axis of rotation so that the immunocyte is bound to the substance so as to be fixed; and
subsequently carrying out a washing operation and determining the immunocyte.

Further, according to the present invention, there is provided an apparatus used in a method of determining a cell surface antigen in a complexed antigen-antibody reaction system, comprising:
a container for holding a first liquid containing an immunocyte having at its surface an immune antigen-antibody complex composed of an antigen and an antibody combined with the antigen;
a substance secured to part of an inner surface of the container, the substance being capable of specifically combining with immunoglobulin;
a second liquid contained in the container together with the first liquid, the second liquid being higher in specific gravity than the first liquid; and
container rotating means for rotating the container in such a manner that the part of the inner surface is disposed most remote from the axis of rotation.

In the determination method of the present invention, a certain immunocyte in the first liquid has at its surface an immune antigen-antibody complex. This immune antigen-antibody complex is composed of an antigen present on the surface of the immunocyte and an immunoglobulin (antibody) corresponding to the antigen and combined with the antigen. The immunocyte having such immune complex floats in the first liquid. When the container having a second liquid higher in specific gravity than the first liquid is rotated, the immunocyte having such immune complex is subjected to a centrifugal force, and enters the second liquid and approaches the substance secured to the inner surface of the container. Then, the substance combines with the Fc portion of the immunoglobulin constituting the immune antigen-antibody complex combined with the immunocyte. Thus, the immunocyte is fixed at the inner surface of the container.

The first liquid contains an immunoglobulin (II) different from the above-mentioned immunoglobulin (I), and an immunocyte (II) different from the above-mentioned immunocyte (I). They are not combined with each other. Even in this case, only the immunocyte (I) can be fixed at the above inner surface. The reason for this will now be described. Since the immunoglobulin (II) is very much smaller than the immunocyte (I), its diffusion speed is low. Therefore, the immunocyte (I) reaches the above substance earlier. Therefore, the two can be distinguished from each other if the rotation of the container is stopped before the immunoglobulin (II) reaches the substance. This is true also with respect to the residual immunoglobulin (I). On the other hand, like the immunocyte (I), the immunocyte (II) also moves toward the substance under the influence of a centrifugal force when the container is rotated. However, the immunocyte (II) does not have immunoglobulin capable of combining with the substance, and therefore is merely abutted against the substance and the inner surface of the container around the substance. The immunocyte (II) can be easily separated from the substance by washing.

In the apparatus of the present invention, the first and second liquids are held in the container, and the container is rotated by the container rotating means. At this time, the immunocyte having at its surface the immune antigen-antibody complex is fixed to the substance secured to the container. The process up to fixation is the same as that described above with respect to the method of the invention.

DESCRIPTION OF THE PREFERRED EMBODIMENTS

A preferred embodiment of a determination method of the present invention, as well as an apparatus used in this method, will now be described.

Figure 1:
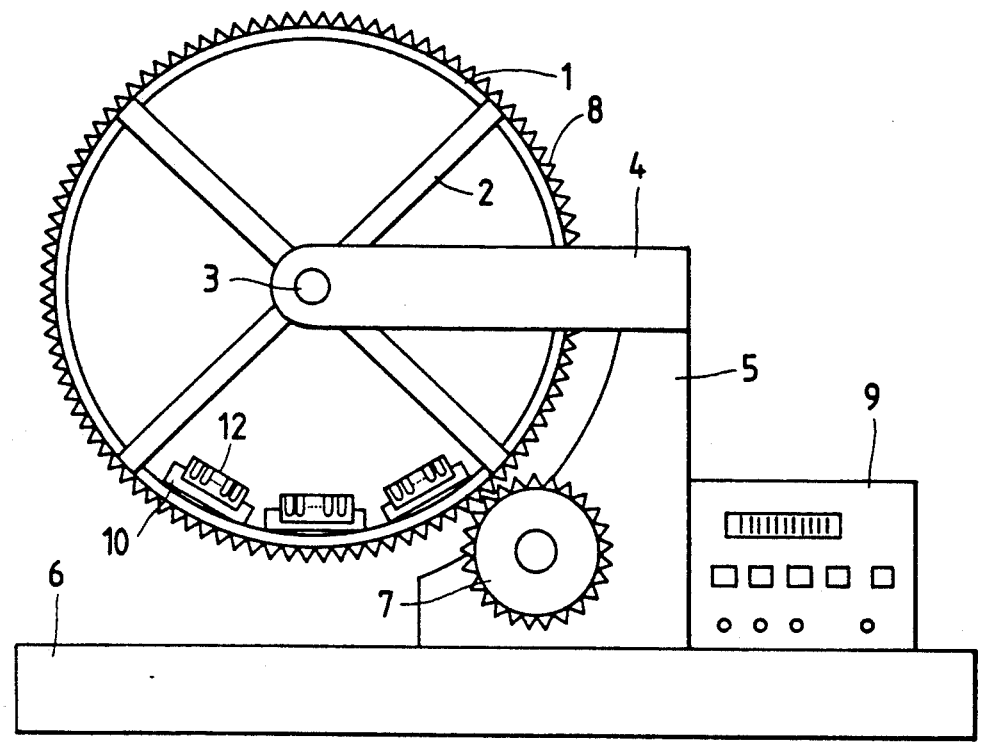
FIG. 1 is a side view showing the overall construction of an apparatus for performing a method of the present invention.
Figure 2:
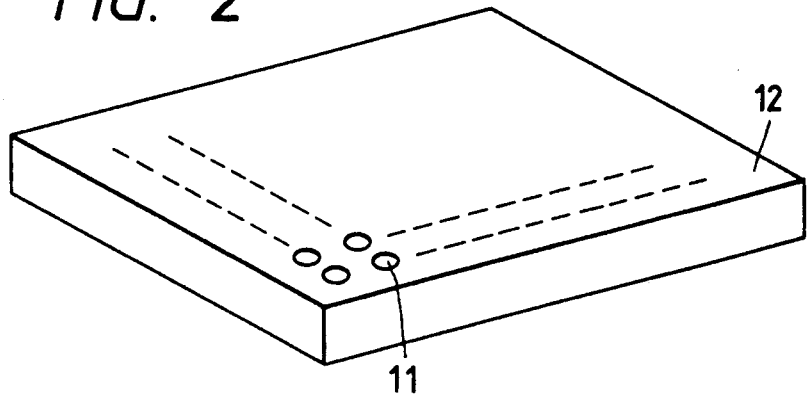
FIG. 2 is an enlarged view of a plate shown in FIG. 1.
Figure 3:
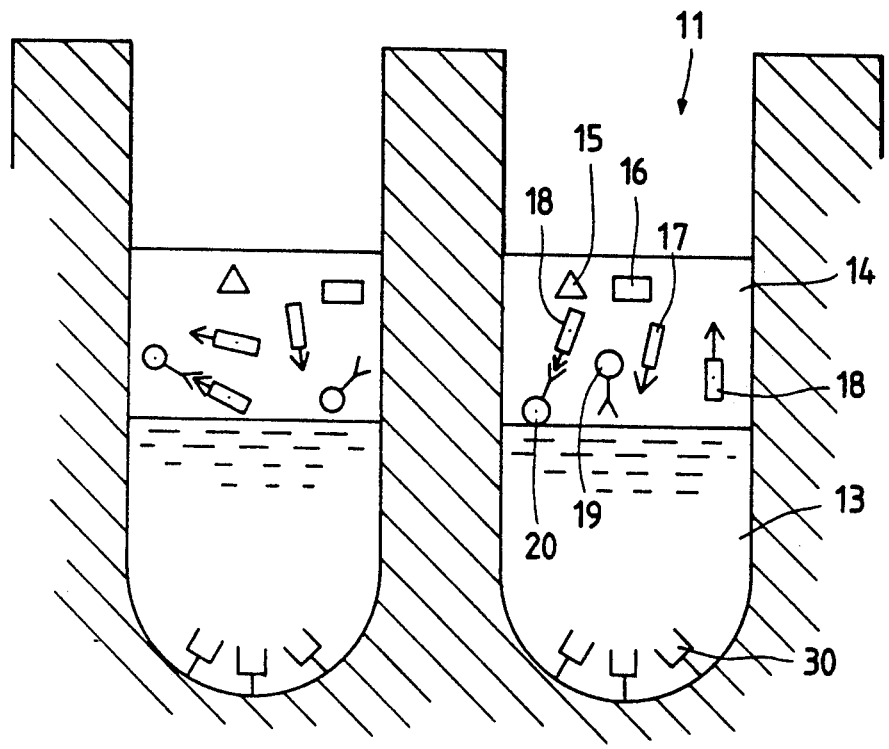
FIG. 3 is a view illustrative of a liquid contained in wells of the plate shown in FIG. 2.

FIG. 1 shows the overall construction of an apparatus of the present invention. A drum 1 is supported on a shaft 3 through four support members 2. The shaft 3 is supported at its opposite ends by a pair of arms 4 so as to be rotatable. The arms 4 are supported by an arm support member 5. The arm support member 5 is fixedly mounted on a base 6. The arm support member 5 has a box-like shape, and contains a motor therein. A gear 7 is mounted on a rotatable shaft of the motor. A gear 8 is formed on the outer periphery of the drum 1, and the gear 8 is in mesh with the gear 7. A controller 9 controls the speed of rotation of the above motor, and is mounted on the base 6. More than one holder 10 is mounted on the inner surface of the drum 1, the holders 10 being disposed adjacent to one another. The holder 10 releasably holds a plate 12 having a number of wells 11 as shown in FIG. 2. As shown in FIG. 3, protein A 30 is secured in layers to the inner bottom surface of each well 11 in a solid state.

In this embodiment, it is intended to fix predetermined lymphocytes contained in a plasma liquid. Therefore, as shown in FIG. 3, a liquid 13 higher in specific gravity than the lymphocyte is contained in each well 11 in the plate 12. The plasma liquid 14 to be examined is held above the liquid 13. The plasma liquid 14 contains serum 15, blood cells 16, A-antibodies 17, B-antibodies 18, A-lymphocytes 19 and B-lymphocytes 20. Here, the serum 15 and the blood cells 16 are blood components which do not directly contribute to an immune reaction. The A-antibodies 17 and the A-lymphocytes 19 are non-specific in the immune reaction, and the B-antibodies 18 and the B-lymphocytes 20 are specific in the immune reaction. More specifically, the B-lymphocyte 20 undergoes an antigen-antibody reaction with part of the B-antibody 18, and combines with the B-antibody 18. In this embodiment, the plasma liquid containing the same lymphocyte is held in the wells 11, and different antibodies are applied to respective ones of the wells 11 so as to determine the lymphocyte subjected to the antigen-antibody reaction. Ninety-six (96) wells 11 are formed in each plate 12. Each well 11 of each plate 12 holds the liquid 13 higher in specific gravity than the plasma liquid 14 and the plasma liquid 14, as shown in FIG. 3. The operator mounts plural plates 12 on the holder 10, as shown in FIG. 1, and operates the controller 9 to rotate the drum 1. The controller 9 controls the rotational speed of the drum 1 from its first rotation to its final rotation so as to maintain the positional relation between the plasma liquid 14 and the liquid 13 in the well 11.

The following phenomenon occurs in the well 11 during the rotation of the drum 1. First, the A-lymphocyte 19 and the B-lymphocyte 20 pass through the liquid 13 and reach the protein A 30. Here, the A-lymphocyte 19 is merely contacted with the protein A 30, but the B-lymphocyte 20 is combined with the B-antibody 18, and the Fc portion of this B-antibody 18 is combined with the protein A 30. On the other hand, the serum 15, the blood cells 16, the A-antibody 17 and B-antibody 18 (the residue which has not been combined with the B-lymphocyte 20) are lower in diffusion speed or in specific gravity than the A-lymphocyte 19 and the B-lymphocyte 20, and therefore still reside at an upper layer portion of the liquid 13 at the time when the A-lymphocyte 19 and the B-lymphocyte 20 reach the protein A 30.

Figure 4:
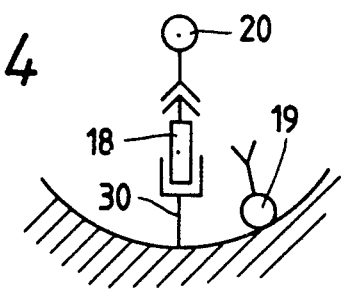
FIG. 4 is a view illustrative of a phenomenon developing in the well.

The controller 9 allows the drum 1 to rotate during a predetermined time period, and thereafter stops its rotation. The operator removes the liquid 13 and the plasma liquid 14 from the well 11 to which the protein A 30 is secured, and the plate 12 is allowed to remain stationary during a predetermined time period. At this time, the B-lymphocyte 20 is arrested by the protein A 30 through the B-antibody 18 in the vicinity of the bottom of the well 11, as shown in FIG. 4, and the A-lymphocyte 19 is in contact with the bottom of the well 11. Then, the operator washes the bottom of the well 11 to remove the A-lymphocyte 19 while allowing the B-lymphocyte 20 to remain there. Thus, the B-lymphocyte 20 is fixed.

In this embodiment, the predetermined lymphocyte in the plasma liquid can be positively determined. Also, the apparatus performing this method can positively determine the predetermined lymphocyte.

In this embodiment, although the substance secured to part of the inner surface of the container is the protein A 30, it may be replaced by any other substance which can specifically combine with the immunoglobulin, such for example as protein G.

In this embodiment, although the immunocyte to be determined is the lymphocyte, it may be replaced by an erythrocyte having an antigen of ABO type, MN type or Rh type, or a blood platelet having a human leukocyte antigen system A (HLA). However, in the case of fixing such immunocyte, it is necessary to beforehand remove from the plasma liquid those immunocytes (for example, lymphocyte) having a higher specific gravity than that of the immunocyte to be fixed.

Figures 5A, 5B, 5C:
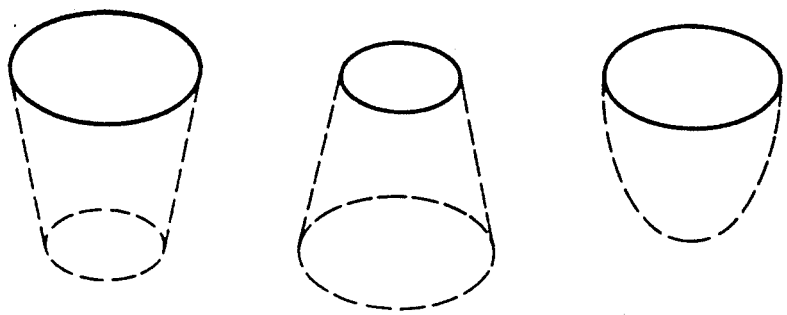
FIGS. 5(a)-5(i) show modified forms of wells.
Figures 5D, 5E, 5F:
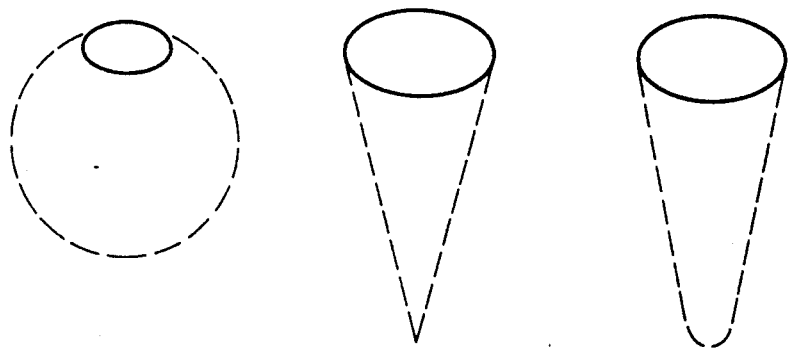
Figures 5G, 5H, 5I:
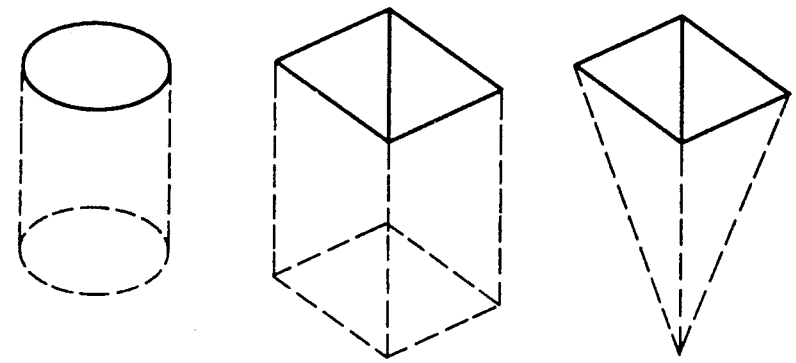

In the apparatus of this embodiment, although the well 11 is cylindrical and has a semi-spherical bottom surface, it can have any other suitable shape such as those shown in FIGS. 5(a) to 5(i). FIG. 5(a) shows a truncated cone-shape, FIG. 5(b) shows an inverted shape of that of FIG. 5(a), FIG. 5(c) shows a semi-oval shape, FIG. 5(d) a spherical shape, FIG. 5(e) shows a conical shape, FIG. 5(f) shows a conical shape having a distal end of an oval shape, FIG. 5(g) shows a cylindrical shape, FIG. 5(h) shows a square cross-section, and FIG. 5(i) shows a pyramid-shape.

In the apparatus of this embodiment, although the plate 12 has a square shape, it may be a circular plate or a polygonal plate. Further, these plates may be stacked one upon another.

Figure 6A:
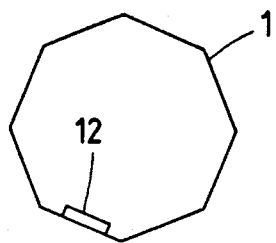
FIGS. 6(a)-6(d) show modifications replacing a drum shown in FIG. 1.
Figure 6B:
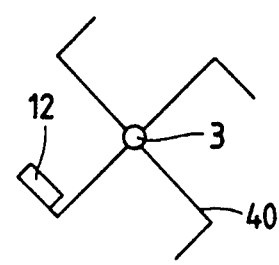
Figure 6C:
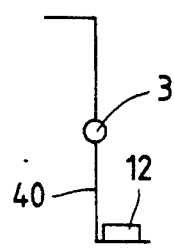
Figure 6D:
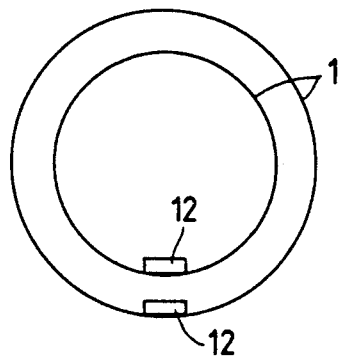

In the apparatus of this embodiment, although the drum is of a cylindrical shape, it may have a polygonal tubular shape as shown in FIG. 6(a), or may be replaced by a plurality of drums coaxially arranged, as shown in FIG. 6(d). Alternatively, as shown in FIGS. 6(b) and 6(c), there may be used support members 40 projecting radially from the shaft 3 so that the plates 12 can be supported respectively on the distal ends of the support members 40.

Figure 7A:
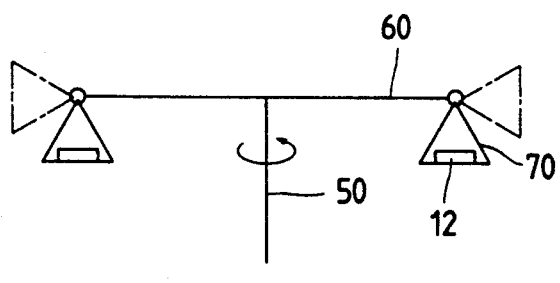
FIGS. 7(a)-7(b) show modified mechanisms for rotating the plates 12 shown in FIG. 1.
Figure 7B:
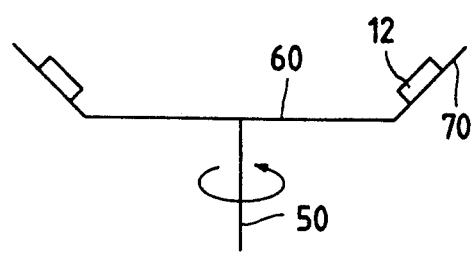

In the apparatus of this embodiment, although each plate 12 is rotated along a circular path along a vertical plane, the plate 12 may be rotated in such a manner as shown in FIGS. 7(a) and 7(b). In FIG. 7(a), a horizontal arm 60 is mounted on a vertical shaft 50, and support members 70 each adapted to support the plate 12 are pivotally connected respectively to the opposite ends of the arm 60. In this case, when the shaft 50 rotates, the support members 70 are gradually inclined under the influence of a centrifugal force, and when the rotational speed becomes high, the support members 70 are disposed at an angle of 90 degrees from their initial position, that is, the vertical plane, as indicated in dot-and-dash lines. In this example, even if the shaft 50 is not rotated at a high speed from the beginning, the positional relation between the liquid 13 and the plasma 14 shown in FIG. 3 can be always maintained. In FIG. 7(b), support members 70 are secured respectively to the opposite ends of the arm 60 in inclined relation to a horizontal plane. In this case, similar effects to those in FIG. 7(a) can be achieved.

In the present invention, without the use of a complement, the immunocyte can be accurately determined while restraining the non-specific reaction. In this case, it is not necessary to accurately carry out pretreatments of the specimen blood, such as the separation of a lymphocyte and serum and the washing-out of a serum protein.

According to the present invention, since the lymphocyte is hardly subjected to damage, the present invention can be used in pretreatments of a specimen in the research of hematology and immunology.

In the present invention, by adjusting the composition and specific gravity of the second liquid, the present invention is applicable to separation, concentration and removal of blood components.

According to the present invention, the automation can be made by a simple apparatus, and therefore cost, time and labor can be saved.

What is claimed is:

1. A cell surface antigen determination method for determining the presence or amount of a specific immunocyte in a sample of an antigen-antibody reaction system, said sample comprising immunocytes carrying said cell surface antigen bound to an antibody specific for said cell surface antigen thereby forming immunocyte complexes, unreacted immunocytes not carrying said cell surface antigen, and unreacted antibody, said method comprising the steps of:
   a) securing to part of an inner surface of a container a substance that specifically binds to the Fc portion of said antibody bound to said cell surface antigen;
   b) introducing (i) a first liquid and (ii) a second liquid into said container, wherein said first liquid comprises said sample and is not in contact with said part of the container to which said substance is fixed and wherein said second liquid has a specific gravity higher than the specific gravity of said first liquid and is in contact with said substance;
   c) rotating said container in such a manner that said part of said inner surface is disposed most remote from the axis of rotation, so that said immunocyte complexes migrate into and through said second liquid to contact and bind to said substance;
   d) removing said first and second liquids;
   e) washing said container to remove unreacted immunocyte, and
   f) determining the presence or the amount of said immunocyte complex fixed to said container as a determination of the presence or amount of the specific immunocyte.

* * * * *